United States Patent
Yamamoto et al.

(10) Patent No.: US 8,703,303 B2
(45) Date of Patent: Apr. 22, 2014

(54) ORGANIC ELECTROLUMINESCENT DEVICE HAVING A LIGHT-EMITTING LAYER COMPRISING A HOST MATERIAL OF TWO OR MORE COMPOUNDS

(75) Inventors: Toshihiro Yamamoto, Kitayushu (JP); Takahiro Kai, Kitakyushu (JP); Masaki Komori, Kitakyushu (JP); Taishi Tsuji, Tsurugashima (JP); Yasuhiro Takahashi, Tsurugashima (JP); Toshinao Yuki, Yonezawa (JP); Yusuke Nakajima, Yonezawa (JP); Tomoaki Hoshi, Yonezawa (JP); Jiro Asaka, Yonezawa (JP)

(73) Assignees: Nippon Steel & Sumikin Chemical Co., Ltd., Tokyo (JP); Pioneer Corporation, Kawasaki-Shi (JP); Tohoku Pioneer Corporation, Tendo-Shi (JP)

( * ) Notice: Subject to any disclaimer, the term of this patent is extended or adjusted under 35 U.S.C. 154(b) by 477 days.

(21) Appl. No.: 12/991,301

(22) PCT Filed: Apr. 30, 2009

(86) PCT No.: PCT/JP2009/058526
§ 371 (c)(1),
(2), (4) Date: Nov. 5, 2010

(87) PCT Pub. No.: WO2009/136596
PCT Pub. Date: Nov. 12, 2009

(65) Prior Publication Data
US 2011/0062862 A1    Mar. 17, 2011

(30) Foreign Application Priority Data

May 8, 2008  (JP) ................................ 2008-122052
May 8, 2008  (JP) ................................ 2008-122053

(51) Int. Cl.
*H01L 51/54* (2006.01)
*C09K 11/06* (2006.01)

(52) U.S. Cl.
USPC ........... 428/690; 428/917; 313/502; 313/504; 257/40

(58) Field of Classification Search
None
See application file for complete search history.

(56) References Cited

U.S. PATENT DOCUMENTS

| 7,993,760 B2 * | 8/2011 | Komori et al. ............... 428/690 |
| 8,062,769 B2 * | 11/2011 | Kai et al. ..................... 428/690 |
| 2007/0090756 A1 | 4/2007 | Okada et al. |
| 2007/0122655 A1 * | 5/2007 | Deaton et al. ................ 428/690 |
| 2007/0212569 A1 | 9/2007 | Je et al. |
| 2009/0302742 A1 | 12/2009 | Komori et al. |
| 2010/0187977 A1 | 7/2010 | Kai et al. |

FOREIGN PATENT DOCUMENTS

| JP | 2007-134677 A | 5/2007 |
| JP | 2007-254737 A | 10/2007 |
| WO | WO 2007/063754 A1 | 6/2007 |
| WO | WO 2008/056746 A1 | 5/2008 |

OTHER PUBLICATIONS

Meerheim et al., "Ultrastable and efficient red organic light emitting diodes with doped transport layers," Applied Physics Letters, vol. 89, pp. 061111-1-061111-3.
Notification of Transmittal of Translation of the International Preliminary Report on Patentability and English translation of the International Preliminary Report on Patentability dated Dec. 23, 2010 for Application No. PCT/JP2009/058526 (Forms PCT/IB/338 and PCT/IPEA/409).
International Search Report for PCT/JP2009/058526, dated Aug. 11, 2009.

* cited by examiner

*Primary Examiner* — Andrew K Bohaty
(74) *Attorney, Agent, or Firm* — Birch, Stewart, Kolasch & Birch, LLP

(57) ABSTRACT

Disclosed is an organic electroluminescent device (organic EL device) that is improved in the luminous efficiency, fully secured of the driving stability, and of a simple structure. The organic EL device comprises a light-emitting layer between an anode and a cathode piled one upon another on a substrate and the said light-emitting layer comprises (A) a phosphorescent dopant whose emission peak wavelength is longer than 600 nm and (B) a host material. The host material contains at least two kinds of compounds selected from two or more kinds of derivatives included in (b1) N-substituted indolocarbazole derivatives, (b2) derivatives of 8-hydroxyquinoline aluminum complex, and (b3) bisindolocarbazole derivatives.

2 Claims, 1 Drawing Sheet

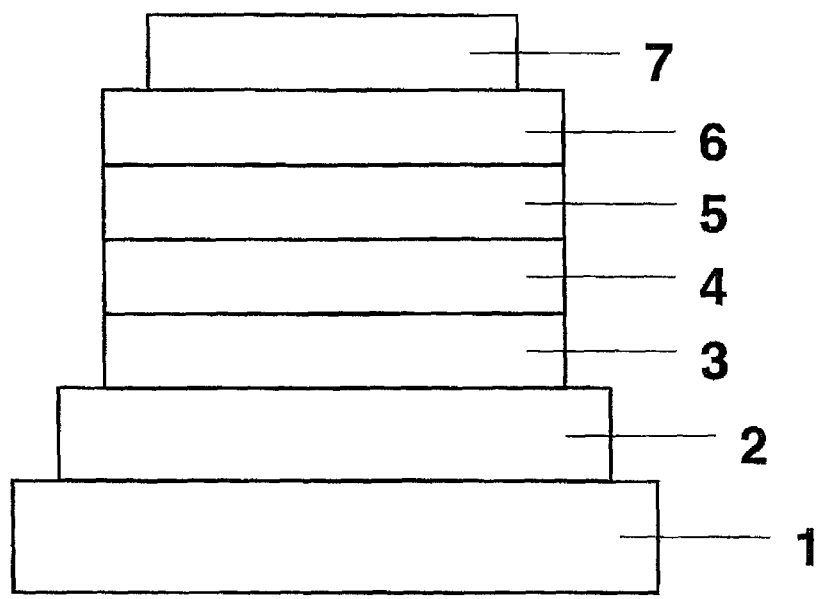

ORGANIC ELECTROLUMINESCENT DEVICE HAVING A LIGHT-EMITTING LAYER COMPRISING A HOST MATERIAL OF TWO OR MORE COMPOUNDS

FIELD OF TECHNOLOGY

This invention relates to a novel organic electroluminescent device (hereinafter referred to as organic EL device) and, more particularly, to an organic EL device that uses a phosphorescent dopant emitting red light and a plurality of host compounds of a specified structure in the light-emitting layer.

BACKGROUND TECHNOLOGY

An organic EL device in the simplest structure is generally constituted of a light-emitting layer and a pair of counter electrodes sandwiching the said light-emitting layer. The device functions by utilizing the following phenomenon; upon application of an electrical field between the electrodes, electrons are injected from the cathode and holes are injected from the anode and the excited state created by recombination of the electrons and holes in the light-emitting layer returns to the ground state with emission of light.

In recent years, organic thin films have been used in the development of organic EL devices. In particular, in order to enhance the luminous efficiency, the kind of electrodes has been optimized for the purpose of improving the efficiency of injecting carriers from the electrodes and a device has been developed in which a hole-transporting layer composed of an aromatic diamine and a light-emitting layer composed of 8-hydroxyquinoline aluminum complex (hereinafter referred to as Alq3) are disposed in thin film between the electrodes. This device has brought about a marked improvement in the luminous efficiency over the conventional devices utilizing single crystals of anthracene and the like and thereafter the developmental works of organic EL devices have been directed toward commercial applications to high-performance flat panels featuring self-luminescence and high-speed response.

In another effort to enhance the luminous efficiency of the device, the use of phosphorescence in place of fluorescence is investigated. The aforementioned device comprising a hole-transporting layer composed of an aromatic amine and a light-emitting layer composed of Alq3 and many other devices utilize fluorescence. The use of phosphorescence, that is, emission of light from the excited triplet state, is expected to enhance the luminous efficiency approximately three times that of the conventional devices utilizing fluorescence (emission of light from the excited singlet state). To achieve this objective, the use of coumarin derivatives and benzophenone derivatives in the light-emitting layer was investigated, but these derivatives merely produced luminance at an extremely low level. Europium complexes were also investigated in trials to utilize the excited triplet state, but they too failed to emit light at high efficiency.

Patent document 1: JP2003-515897 A
Patent document 2: JP2001-313178 A
Patent document 3: JP2002-305083 A
Patent document 4: JP2003-142264 A
Patent document 5: JP 11-162650 A
Patent document 6: JP 11-176578 A
Non-patent document 1: APPLIED PHYSICS LETTERS, Vol. 75(1), pp. 4-6, 1999
Non-patent document 2: APPLIED PHYSICS LETTERS, Vol. 78(11), pp. 1622-1624, 2001
Non-patent document 3: APPLIED PHYSICS LETTERS, Vol. 89, p. 061111-1-3, 2006

A large number of phosphorescent dopants useful for the light-emitting layer of an organic EL device are disclosed in patent document 1 and elsewhere. A typical example is tris(2-phenylpyridine)iridium complex (hereinafter referred to as Ir(ppy)3).

A substance proposed as a host material for the light-emitting layer of an organic EL device is 4,4'-bis(N-carbazolyl)biphenyl (hereinafter referred to as CBP), a carbazole compound cited in non-patent documents 1 and 2 and patent document 2 and elsewhere. From the viewpoint of triplet exciton confinement, CBP is used widely as a host material for Ir(ppy)3, a phosphorescent material emitting green light, and for octaethylporphyrin platinum complex (hereinafter referred to as PtOEP), a phosphorescent material emitting red light.

However, an organic EL device comprising CBP as a host material in the light-emitting layer has faced a problem that the barrier to injection of holes from the hole-transporting layer composed of an arylamine compound into the light-emitting layer tends to become higher and the driving voltage becomes higher.

On the other hand, CBP has a property of allowing holes to flow more easily than electrons; hence, excess holes tend to flow out to the side of the electron-transporting layer when CBP is used and this is one cause for lowering of the luminous efficiency. As a means to solve this problem, a hole-blocking layer is provided between the light-emitting layer and the electron-transporting layer as done, for example, in patent document 3. The hole-blocking layer thus provided accumulates holes efficiently in the light-emitting layer and improves the probability of recombination of holes and electrons in the light-emitting layer thereby achieving the object of enhancing the luminous efficiency. The hole-blocking materials in general use at present include 2,9-dimethyl-4,7-diphenyl-1,10-phenanthroline (hereinafter referred to as BCP) and p-phenylphenolato-bis(2-methyl-8-quinolinolato-N1,O8) aluminum (hereinafter referred to as BAlq). These materials are capable of preventing electrons and holes from recombining in the electron-transporting layer. However, BCP lacks reliability as a hole-blocking material on account of its tendency to crystallize easily even at room temperature and a device containing BCP shows an extremely short lifetime. On the other hand, BAlq has a Tg of approximately 100° C. and a device containing it is reported to show a relatively long lifetime; however, the hole-blocking ability of BAlq is not sufficient and the luminous efficiency from Ir(ppy)3 becomes lower.

Further, it is reported in patent document 4 that BAlq is applicable as a host material for a light-emitting layer comprising a phosphorescent material emitting red light. The use of BAlq as a host material produces an effect of attaining high efficiency with no need to provide a hole-blocking layer between the light-emitting layer and the electron-transporting layer. Thus, the device would be freed from the unstable factors attributable to the hole-blocking material and might be expected to improve in the lifetime. However, BAlq has a property of hindering the flow of holes and, besides, the light-emitting layer must be made relatively thick when a hole-blocking layer is omitted and the problem here is a rise in the driving voltage.

Still further, it is reported in non-patent document 3 that 4,4'-bis[(N-1-naphthyl)-N-phenylamino]biphenyl (hereinafter referred to as NPB), a material in widespread use as a hole-transporting material, is applicable as a host material for a light-emitting layer comprising a phosphorescent material emitting red light. The use of NPB as a host material in the light-emitting layer produces an effect of eliminating the barrier to injection of holes from the hole-transporting layer into the light-emitting layer and holding the driving voltage at a low level. However, the problem with arylamine compounds, typically NPB, has been that the substituents attached to their nitrogen atom tend to move easily due to the molecular structure of these compounds thereby increasing the probability of nonradiative deactivation of triplet excitons and, as a result, the efficiency becomes lower. According to non-patent document 3, an attempt is made to enhance the luminous efficiency by adding an electron-absorbing material to the hole-injecting layer and an electron-donating material to the electron-transporting layer and raising the density of holes and electrons in the light-emitting layer.

Further, the indolocarbazole compounds disclosed in patent documents 5 and 6 are recommended for use as a hole-transporting material and are reputed to be stable. However, the documents do not teach their use as a phosphorescent host material.

DISCLOSURE OF THE INVENTION

The Problems to be Solved by the Invention

In applications of organic EL devices to display devices such as flat panel displays, it is necessary to enhance the luminous efficiency of the device and, at the same time, to fully secure the driving stability of the device. Under the aforementioned circumstances, an object of this invention is to provide an organic EL device of high efficiency, good driving stability, and practical usefulness. Another object of this invention is to provide a phosphorescent organic EL device emitting red light.

Means to Solve the Problems

The inventors of this invention have conducted intensive studies, found as a result that the use of a combination of plural compounds of a specified structure in the light-emitting layer of an organic EL device can solve the aforementioned problems, and completed this invention.

This invention relates to an organic electroluminescent device comprising a light-emitting layer between an anode and a cathode piled one upon another on a substrate wherein the said light-emitting layer comprises (A) a phosphorescent dopant whose emission peak wavelength is longer than 600 nm and (B) a host material and the said host material comprises at least two kinds of compounds selected from (b1) a compound represented by the following general formula (1), (b2) a compound represented by the following general formula (2), and (b3) a compound represented by the following general formula (3).

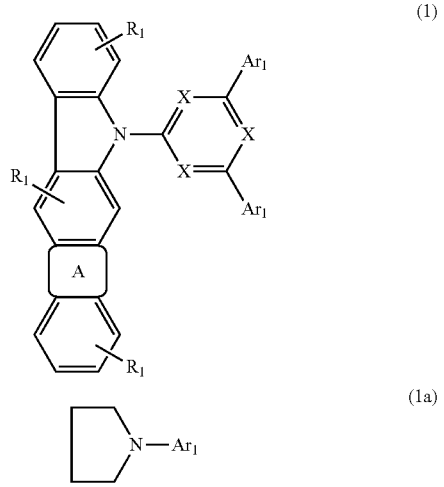

In general formula (1), ring A is a heterocyclic ring fused to the adjacent rings and represented by formula (1a); X is independently CR or N and at least one of Xs is N; $Ar_1$ is independently a substituted or unsubstituted aromatic hydrocarbon or aromatic heterocyclic group of 3 to 24 carbon atoms; each of R and $R_1$ is independently hydrogen, an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an aryloxy group, an alkylthio group, an alkylsulfonyl group, a haloalkyl group, a hydroxyl group, an amide group, or a substituted or unsubstituted aromatic hydrocarbon or aromatic heterocyclic group of 3 to 24 carbon atoms.

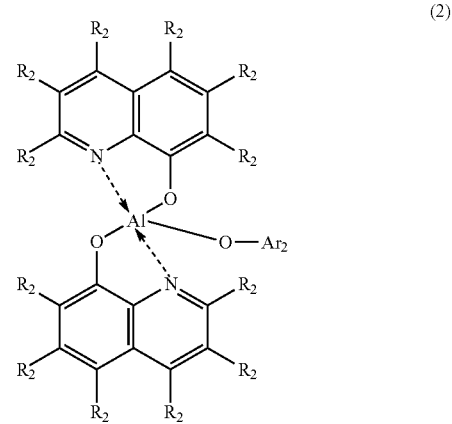

In general formula (2), $Ar_2$ is a substituted or unsubstituted aromatic hydrocarbon group of 6 to 24 carbon atoms and $R_2$ is independently hydrogen or an alkyl group of 1 to 12 carbon atoms.

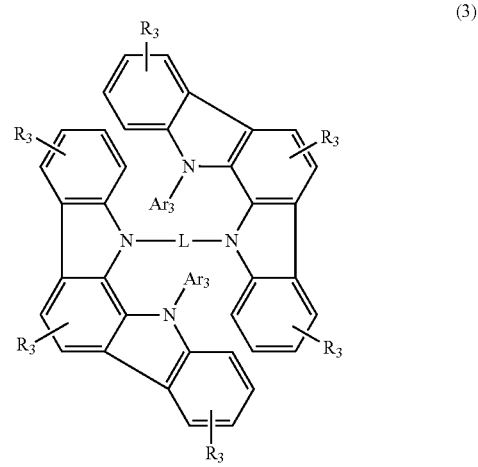

In general formula (3), $Ar_3$ is independently a substituted or unsubstituted aromatic hydrocarbon or aromatic heterocyclic group of 3 to 24 carbon atoms; L is a divalent substituted or unsubstituted aromatic hydrocarbon or aromatic heterocyclic group of 3 to 24 carbon atoms; $R_3$ is independently hydrogen, an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an aryloxy group, an alkylthio group, an alkylsulfonyl group, a haloalkyl group, a hydroxyl group, an amide group, or a substituted or unsubstituted aromatic hydrocarbon or aromatic heterocyclic group of 3 to 24 carbon atoms.

Of the compounds represented by general formula (1), a compound represented by the following general formula (4) is preferred.

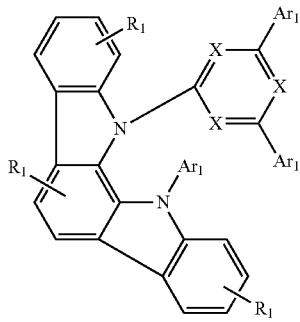

(4)

In general formula (4), X, Ar$_1$, and R$_1$ respectively have the same meaning as X, Ar$_1$, and R$_1$ in general formula (1).

The host material to be used in an organic electroluminescent device in this invention is a combination of at least two kinds of compounds selected from the compounds represented by general formula (1), the compounds represented by general formula (2), and the compounds represented by general formula (3). The following combinations are possible: (1) a compound represented by general formula (1) and a compound represented by general formula (2); (2) a compound represented by general formula (1) and a compound represented by general formula (3); (3) a compound represented by general formula (2) and a compound represented by general formula (3); and (4) a compound represented by general formula (1), a compound represented by general formula (2), and a compound represented by general formula (3). Here, a compound represented by general formula (1) may consist of either a single compound or two or more compounds represented by general formula (1) and the same holds for a compound represented by general formula (2) or (3).

In this invention, the compound represented by general formula (3) is preferably a compound represented by the following general formula (5). In general formula (5), Ar$_2$ and R$_2$ respectively have the same meaning as Ar$_3$ and R$_3$ in general formula (3).

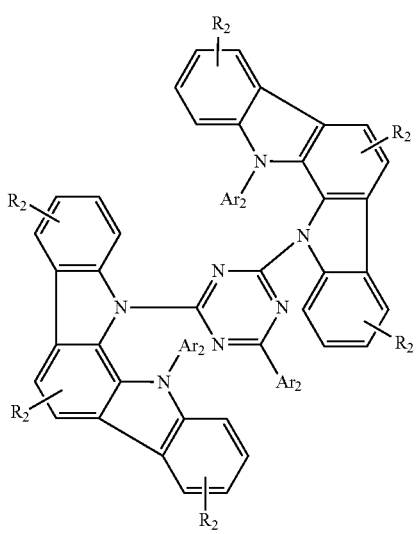

(5)

BRIEF DESCRIPTION OF THE DRAWING

FIG. 1 shows the cross section of an example of an organic EL device.

PREFERRED EMBODIMENTS OF THE INVENTION

An organic electroluminescent device according to this invention comprises a light-emitting layer comprising (A) a phosphorescent dopant and (B) a host material between an anode and a cathode piled one upon another on a substrate. Here, the phosphorescent dopant shows an emission peak wavelength longer than 600 nm and the host material contains at least two kinds of compounds selected from the compounds represented by the aforementioned general formulas (1) to (3). In the following account, a compound represented by general formula (1) will occasionally be abbreviated to a compound of general formula (1) or compound-1. Likewise, a compound represented by general formula (2) or (3) will be abbreviated to compound-2 or compound-3. Furthermore, as a compound of general formula (1) includes a compound of general formula (4) in concept, the former serves as a representative of the two wherever necessary. Likewise, as a compound of general formula (3) includes a compound of general formula (5) in concept, the former serves as a representative of the two. The light-emitting layer comprises at least two kinds of compounds selected from the group of compound-1, compound-2, and compound-3 as a host material.

Thus, one example of preferable host materials to be incorporated in the light-emitting layer contains at least one kind each of compound-1 and compound-2. Another example contains at least one kind each of compound-1 and compound-3. A further example contains at least one kind each of compound-2 and compound-3.

In the aforementioned general formula (1), ring A is a heterocyclic ring fused to the adjacent rings and represented by formula (a1) and each of three Xs is independently CR or N and at least one of Xs is N, preferably two Xs are Ns, more preferably three Xs are Ns. Of the compounds represented by general formula (1), the compounds represented by the aforementioned general formula (4) are preferred. Here, R has the same meaning as R$_1$ to be explained below and it is preferably hydrogen.

In general formulas (1) and (4), Ar$_1$ is independently a substituted or unsubstituted aromatic hydrocarbon or aromatic heterocyclic group of 3 to 24 carbon atoms. Preferable examples of the unsubstituted aromatic hydrocarbon groups include a phenyl group, a naphthyl group, a phenanthryl group, and an anthracenyl group. Preferable examples of unsubstituted aromatic heterocyclic groups include a pyridyl group, a pyrimidyl group, a triazyl group, an imidazolyl group, a thienyl group, and a carbazolyl group. In the case where these aromatic hydrocarbon or aromatic heterocyclic groups possess substituents, the preferable substituents include an alkyl group of 1 to 6 carbon atoms, an alkoxyl group of 1 to 6 carbon atoms, an aryloxy group of 6 to 12 carbon atoms, an alkylthio group, a substituted amino group, an acetyl group, a phenyl group, a biphenylyl group, a terphenylyl group, a naphthyl group, a pyridyl group, a pyrimidyl group, a triazyl group, an imidazolyl group, a thienyl group, and a carbazolyl group.

The group R$_1$ is independently hydrogen, an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an aryloxy group, an alkylthio group, an alkylsulfonyl group, a haloalkyl group, a hydroxyl group, an amide group, or a substituted or unsubstituted aromatic hydrocarbon or aromatic heterocyclic group of 3 to 24 carbon atoms. Preferred are an alkyl group of 1 to 6 carbon atoms, an alkoxyl group of 1 to 6 carbon atoms, an aryloxy group of 6 to 12 carbon atoms, an alkylthio group, a substituted amino group, an acetyl group, a phenyl group, a biphenylyl group, a terphenylyl group, a naphthyl group, a pyridyl group, a pyrimidyl group, a triazyl group, an imidazolyl group, a thienyl group, and a carbazolyl group. In the case where the aromatic hydrocarbon or aromatic heterocyclic groups possess substituents, preferable substituents include those cited in the explanation of $Ar_1$.

In the aforementioned general formula (2), $Ar_2$ is a substituted or unsubstituted aromatic hydrocarbon group of 6 to 24 carbon atoms and preferable examples include a phenyl group, a naphthyl group, a phenanthryl group, and an anthracenyl group. In the case where the aromatic hydrocarbon groups possess substituents, preferable substituents include an alkyl group of 1 to 6 carbon atoms and an aromatic hydrocarbon group of 6 to 24 carbon atoms. Examples of such alkyl and aromatic hydrocarbon groups include a methyl group, an ethyl group, an isopropyl group, a t-butyl group, a phenyl group, a biphenylyl group, a terphenylyl group, a naphthyl group, a phenanthryl group, and an anthracenyl group.

The group $R_2$ is independently hydrogen or an alkyl group of 1 to 12 carbon atoms and $R_2$ is preferably hydrogen or an alkyl group of 1 to 6 carbon atoms. Examples of the alkyl group include a methyl group, an ethyl group, an isopropyl group, and a t-butyl group.

In the aforementioned general formula (3), $Ar_3$ is independently a substituted or unsubstituted aromatic hydrocarbon or aromatic heterocyclic group of 3 to 24 carbon atoms and preferable examples of the unsubstituted aromatic hydrocarbon groups include a phenyl group, a naphthyl group, a phenanthryl group, and an anthracenyl group. Preferable examples of the unsubstituted aromatic heterocyclic groups include a pyridyl group, a pyrimidyl group, a triazyl group, an imidazolyl group, a thienyl group, and a carbazolyl group. In the case where these aromatic hydrocarbon or aromatic heterocyclic groups possess substituents, preferable substituents include an alkyl group of 1 to 6 carbon atoms, an alkoxyl group of 1 to 6 carbon atoms, an aryloxy group of 6 to 12 carbon atoms, an alkylthio group, a substituted amino group, an acetyl group, a phenyl group, a biphenylyl group, a terphenylyl group, a naphthyl group, a pyridyl group, a pyrimidyl group, a triazyl group, an imidazolyl group, a thienyl group, and a carbazolyl group.

The group L is a divalent substituted or unsubstituted aromatic hydrocarbon or aromatic heterocyclic group of 3 to 24 carbon atoms. Preferable examples include the divalent groups formed by removing two hydrogen atoms from single-ring or fused-ring compounds such as benzene, biphenyl, naphthalene, phenanthrene, anthracene, fluorene, imidazole, pyrazole, pyridine, pyrazine, pyrimidine, pyridazine, indolizine, isoindole, indazole, purine, quinoline, isoquinoline, naphthyridine, quinoxaline, quinazoline, carbazole, phenanthridine, acridine, perimidine, phenazine, triazole, benzimidazole, and benzotriazole. More preferable are the divalent groups formed by removing two hydrogen atoms from benzene, biphenyl, naphthalene, pyridine, pyrimidine, pyrazine, triazine, and carbazole. In the case where the aromatic hydrocarbon or aromatic heterocyclic groups possess substituents, preferable substituents include those cited in the explanation of $Ar_1$.

The group $R_3$ is independently hydrogen, an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an aryloxy group, an alkylthio group, an alkylsulfonyl group, a haloalkyl group, a hydroxyl group, an amide group, or a substituted or unsubstituted aromatic hydrocarbon or aromatic heterocyclic group of 3 to 24 carbon atoms. Preferred are an alkyl group of 1 to 6 carbon atoms, an alkoxyl group of 1 to 6 carbon atoms, an aryloxy group of 6 to 12 carbon atoms, an alkylthio group, a substituted amino group, an acetyl group, a phenyl group, a biphenylyl group, a terphenylyl group, a naphthyl group, a pyridyl group, a pyrimidyl group, a triazyl group, an imidazolyl group, a thienyl group, and a carbazolyl group. In the case where the aromatic hydrocarbon or aromatic heterocyclic groups possess substituents, preferable substituents include those cited in the explanation of $Ar_1$.

As described above, the host material to be incorporated in the light-emitting layer of an organic electroluminescent device according to this invention is composed in several ways as follows: (1) a case where the host material contains a compound of general formula (1) and a compound of general formula (2); (2) a case where the host material contains a compound of general formula (1) and a compound of general formula (3); (3) a case where the host material contains a compound of general formula (2) and a compound of general formula (3); and (4) a case where the host material contains a compound of general formula (1), a compound of general formula (2), and a compound of general formula (3). The aforementioned cases (1) to (4) are roughly divided into a group that contains a compound of general formula (1) as an essential component and a group that does not contain a compound of general formula (1) and contains a compound of general formula (2) and a compound of general formula (3) as essential components. The aforementioned cases (1), (2), and (4) belong to the former while the aforementioned case (3) belongs to the latter.

The mixing ratio of these compounds is not limited. However, from the viewpoint of the driving voltage, luminous efficiency, and lifetime, the ratio is (1-99):(1-99), preferably (10-90):(10-90), in the case where two kinds of compounds are selected from a compound of general formula (1), a compound of general formula (2), and a compound of general formula (3). The ratio is (1-98):(1-98):(1-98), preferably (10-80):(10-80):(10-80), in the case where three kinds of compounds are selected from a compound of general formula (1), a compound of general formula (2), and a compound of general formula (3).

In the aforementioned cases of (1), (2), and (4), the mixing ratio of these compounds is not limited. Designating the weight of a compound of general formula (1) (or the sum of weight when two or more compounds of general formula (1) are used) as b1 and the weight of a compound of general formula (2) or (3) (or the sum of weight when two or more compounds of general formula (2) or (3) are used) as b2, the ratio of b1 to the sum of b1 and b2 is preferably in the range of 0.1-99 wt %, more preferably in the range of 20-90 wt %, from the viewpoint of the driving voltage, luminous efficiency, and lifetime. The properties of low driving voltage and long lifetime, characteristic of a compound of general formula (1), are not manifested when the ratio is 0.1 wt % or less while the effect for enhancing the luminous efficiency by means of mixing is not pronounced when the ratio is 99 wt % or more. Further, as for a compound of general formula (2) or a compound of general formula (3), one of them alone or both of them may be used, respectively as a single compound or as a mixture of plural compounds.

In the aforementioned case (3), the mixing ratio of a compound of general formula (2) and a compound of general formula (3) is not limited. However, from the viewpoint of the driving voltage, luminous efficiency, and lifetime, the weight of a compound of general formula (2) to the sum of the weights of a compound of general formula (2) and a compound of general formula (3) is preferably in the range of 0.1-99 wt %, more preferably in the range of 20-90 wt %. The properties of low driving voltage and long lifetime, characteristic of a compound of general formula (2), do not improve when the ratio is 0.1 wt % or less while the effect of enhancing the luminous efficiency is not pronounced when the ratio is 99 wt % or more.

As a host material to be incorporated in the light-emitting layer, a compound of general formula (1) and a compound of general formula (2) or (3) may be mixed in advance before use or they may be co-vacuum-deposited during formation of the light-emitting layer. Likewise, a compound of general formula (2) and a compound of general formula (3) may be mixed in advance before use or they may be co-vacuum-deposited during formation of the light-emitting layer.

The compounds represented by general formulas (1) to (3) and by general formulas (4) and (5) to be incorporated in the organic EL device of this invention can be prepared easily by one of known methods. For example, a compound represented by general formula (1) or (4) can be prepared by a sequence of reactions illustrated below with reference to a synthetic example described in Synlett., 2005, No. 1, pp. 42-48.

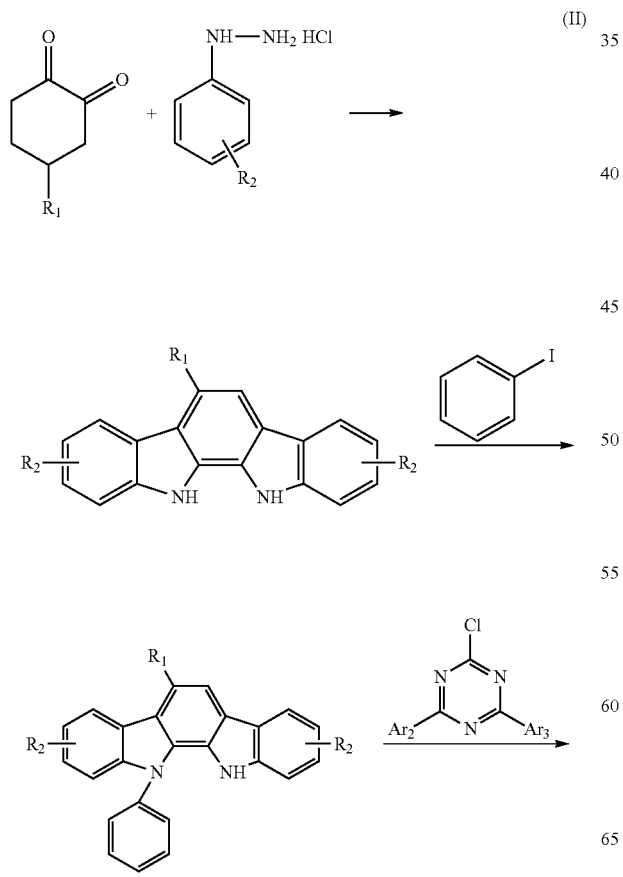

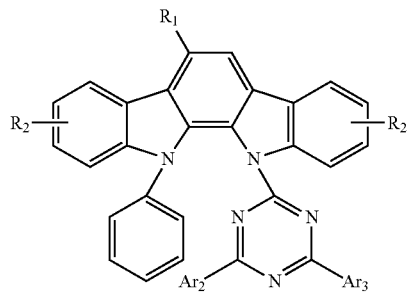

A compound represented by general formula (2) can be prepared by a sequence of reactions illustrated below with reference to a synthetic example described in JP Hei 4-206685 A.

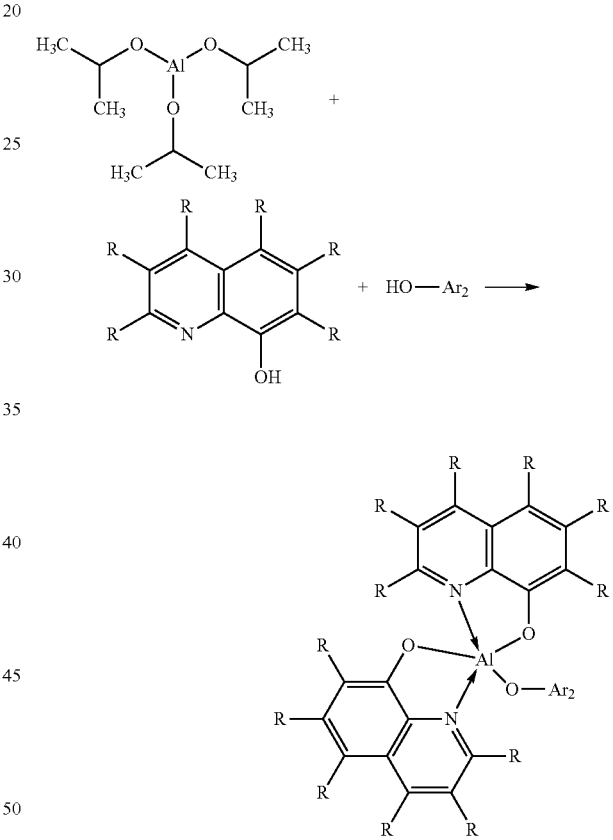

A compound represented by general formula (3) can be prepared by a sequence of reactions illustrated below with reference to a synthetic example described in Tetrahedron, 1991, Vol. 47, No. 37, pp. 7739-7750.

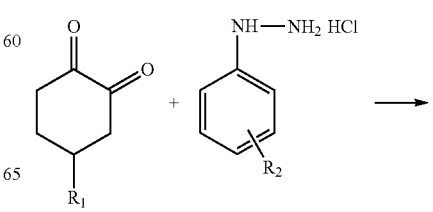

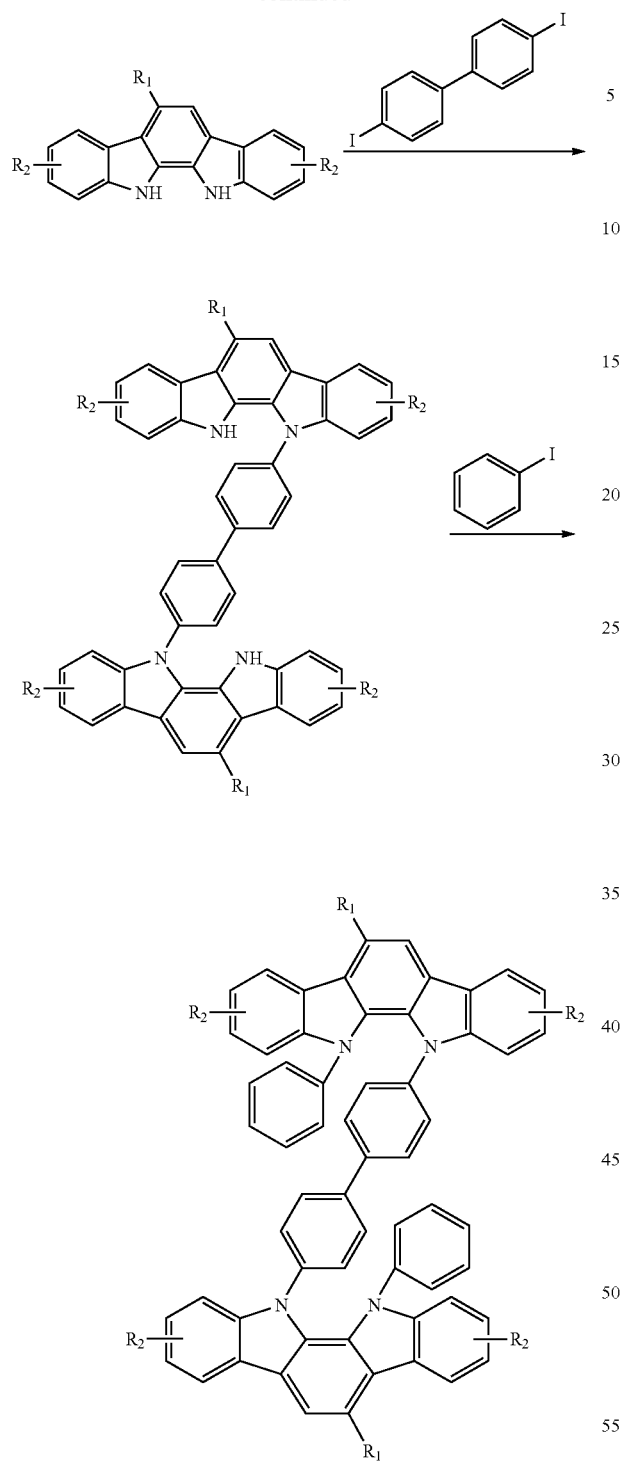

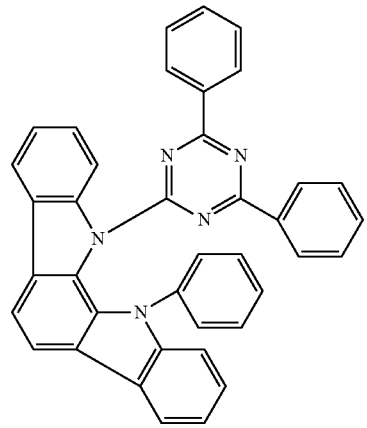

1-1

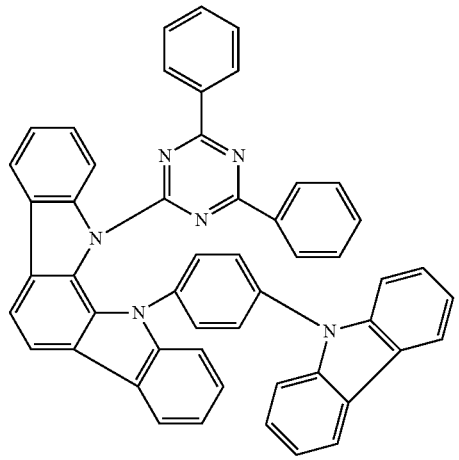

1-2

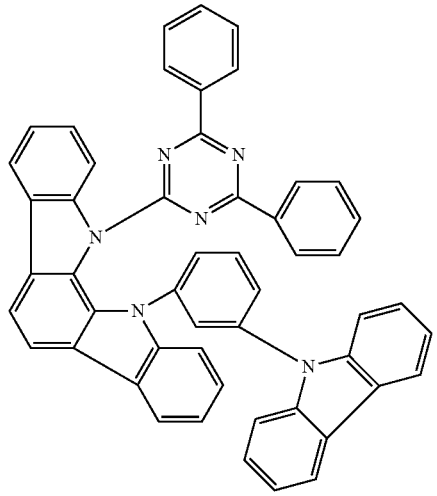

1-3

Preferable examples of the compounds represented by general formula (1) or general formulas (2) and (3) are shown below, but are not limited thereto. Here, Compound 1-1 to Compound 1-8 are examples of the compounds represented by general formula (1), Compound 2-1 to Compound 2-8 are examples of the compounds represented by general formula (2), and Compound 3-1 to Compound 3-8 are examples of the compounds represented by general formula (3).

1-4
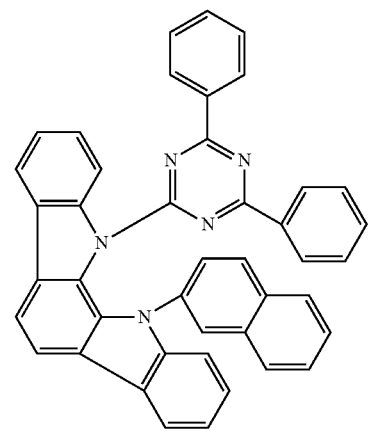
1-5
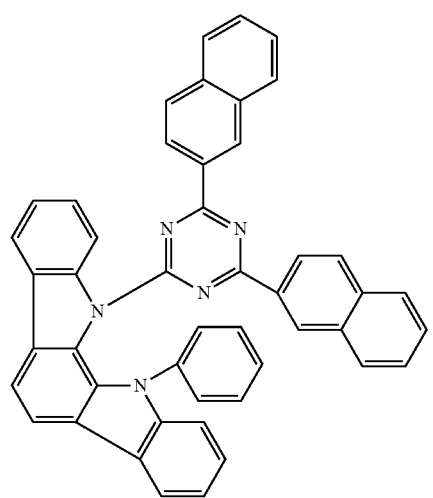
1-6
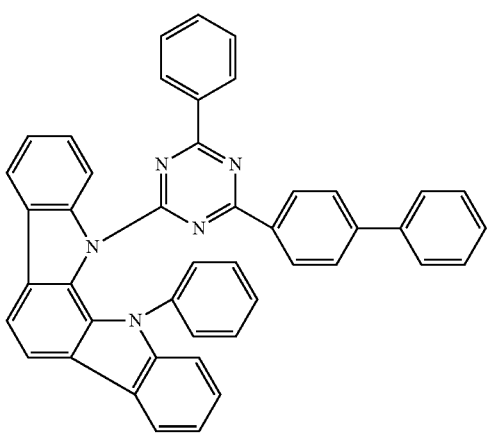
1-7
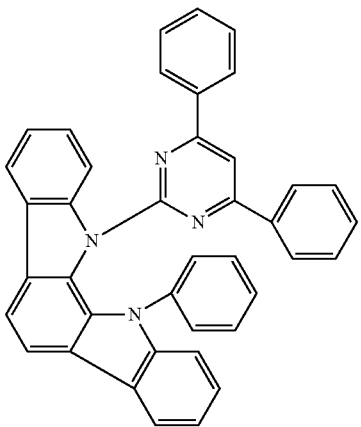
1-8
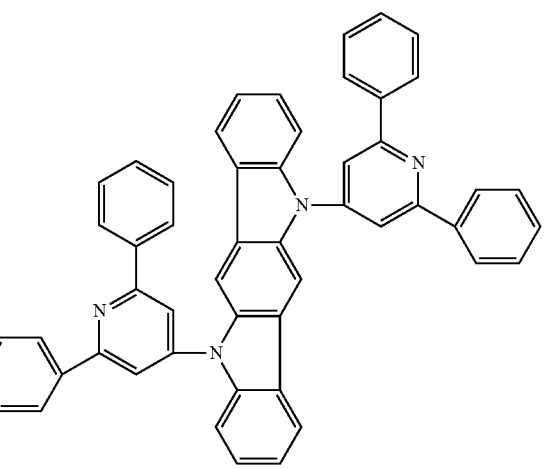
2-1
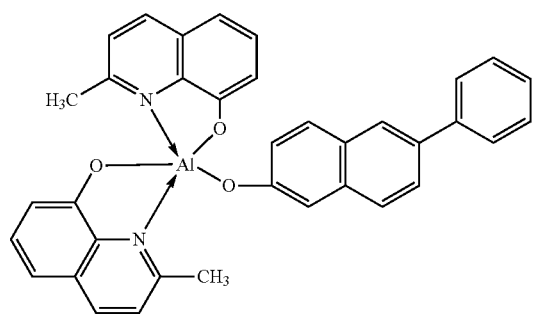
2-2
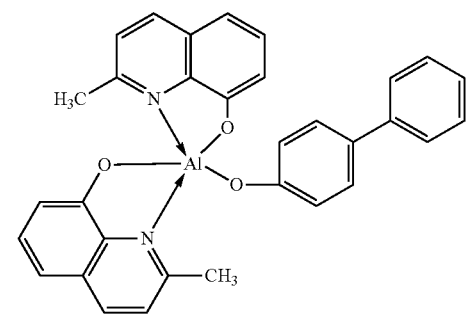

2-3
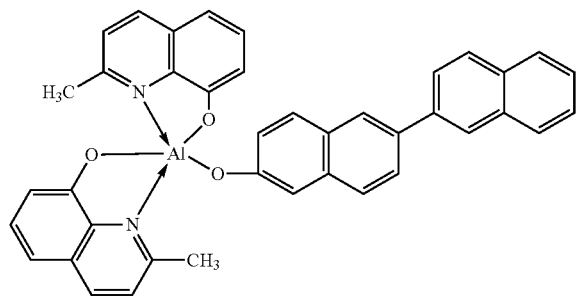
2-4
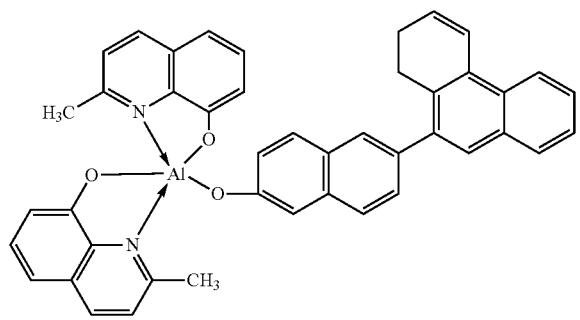
2-5
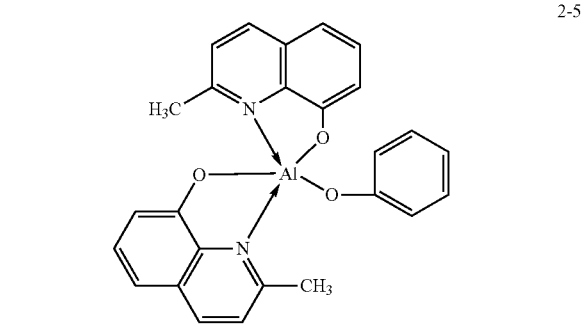
2-6
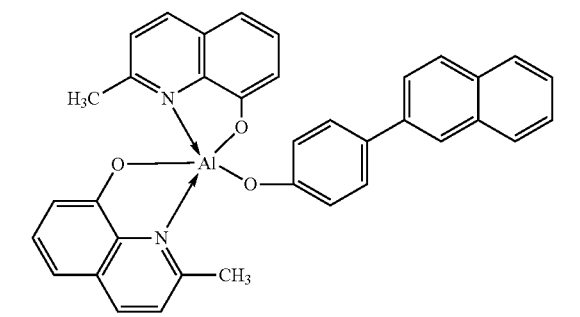
2-7
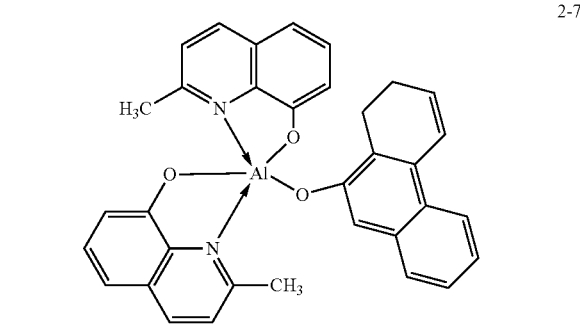
2-8
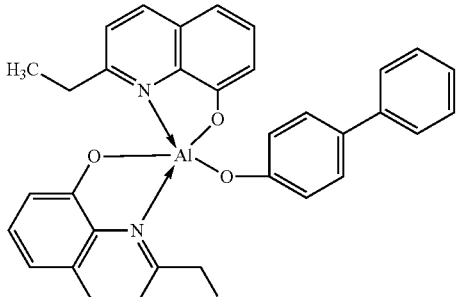
3-1
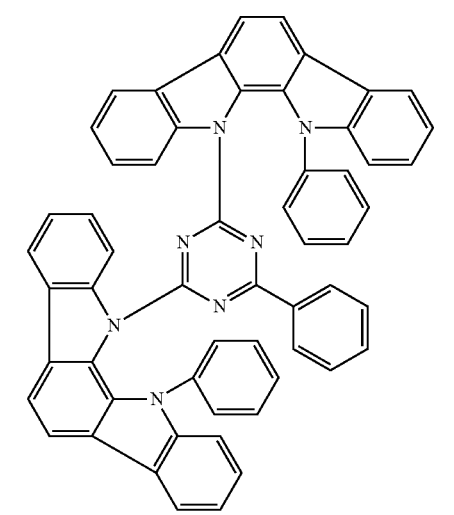
3-2
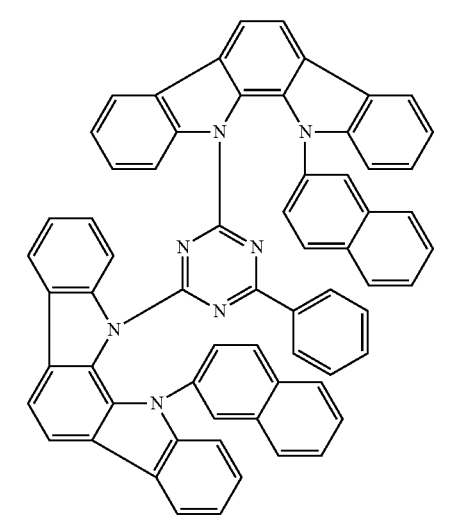

3-3
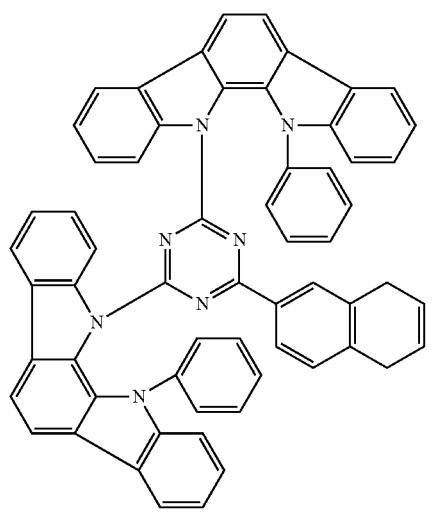
3-4
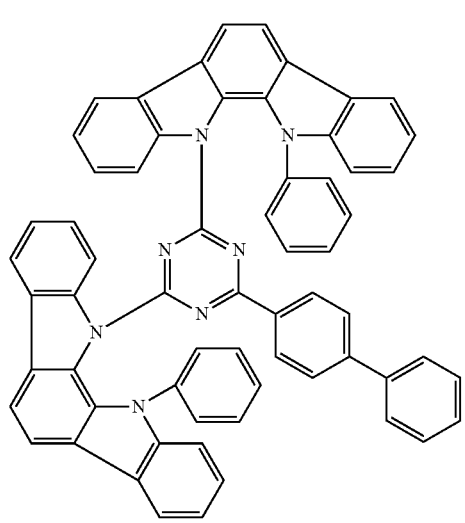
3-5
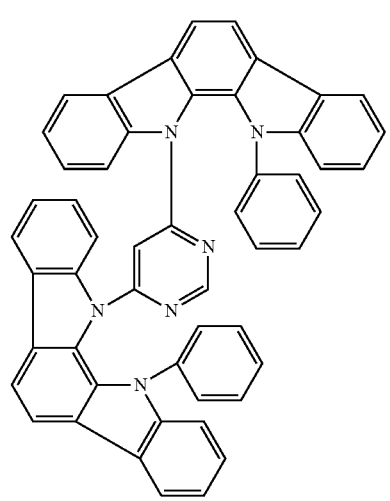
3-6
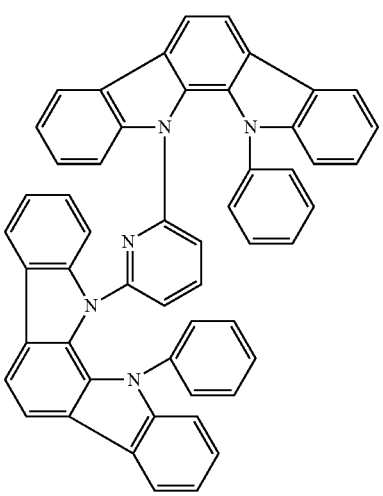
3-7
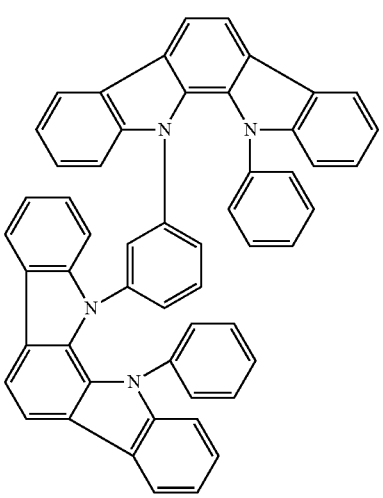
3-8
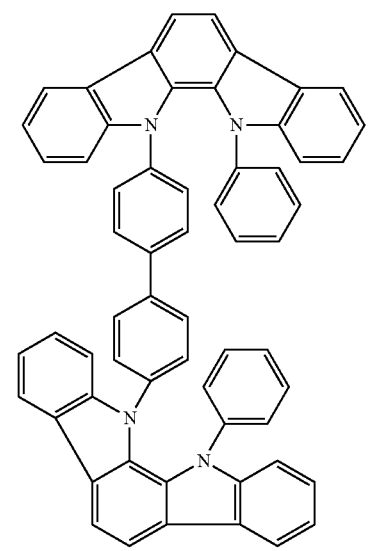
The light-emitting layer comprises a phosphorescent dopant whose emission peak wavelength is longer than 600 nm together with the aforementioned host material. The maximum emission wavelength of the dopant is preferably 600-800 nm. When the wavelength is shorter than 600 nm, yellow light is emitted. When the wavelength is longer than 800 nm, infrared light is emitted.

The materials for phosphorescent dopants preferably include organic metal complexes containing at least one metal selected from ruthenium, rhodium, palladium, silver, rhenium, osmium, iridium, platinum, and gold. Such organic metal complexes are well known in the aforementioned patent documents and elsewhere and a suitable complex can be selected from them and used in this invention.

The aforementioned phosphorescent dopants include complexes containing a noble metal element such as Ir in the center, typically Ir(piq)3, and complexes such as PtOEt. Examples of these complexes are shown below, but are not limited thereto.

4-1
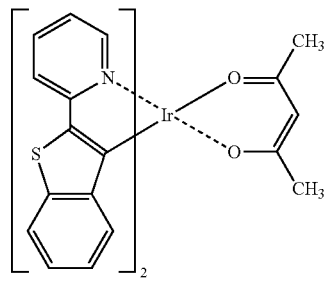

4-2
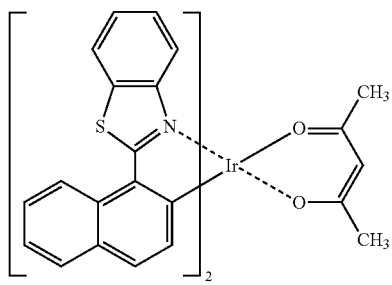

4-3
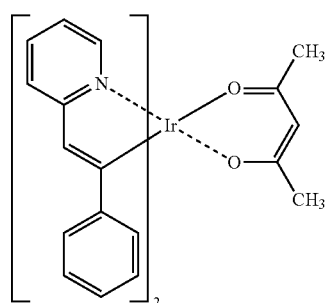

4-4
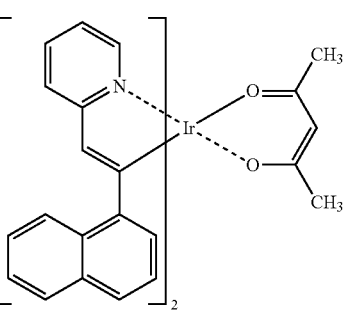

4-5
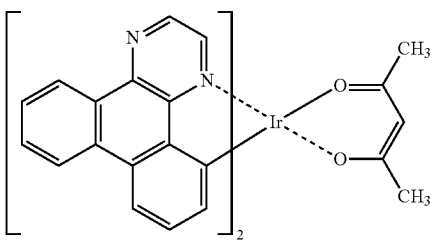

4-6
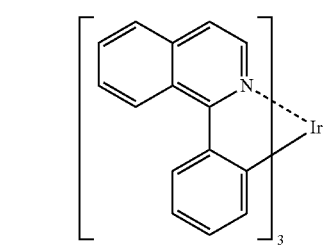

4-7
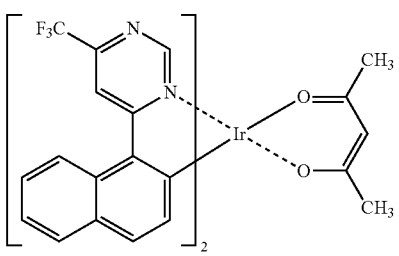

4-8
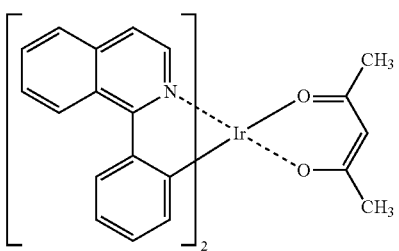

4-9
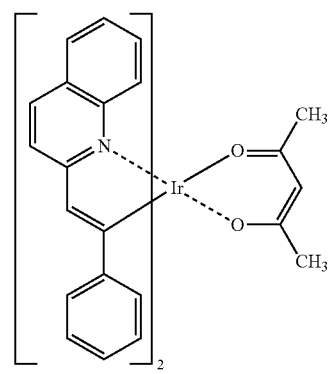

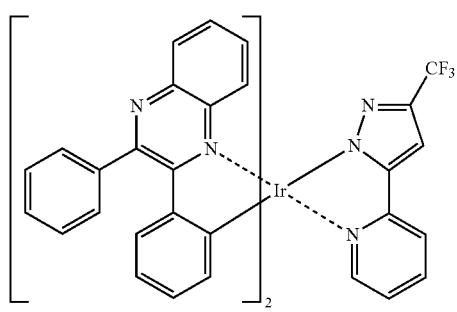
4-10
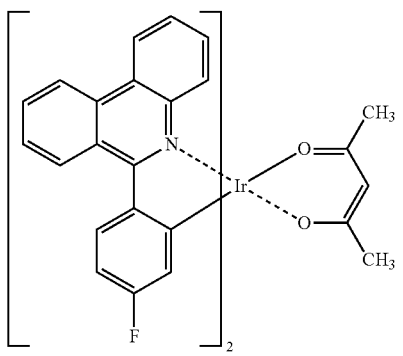
4-11
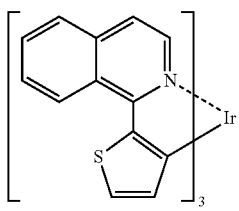
4-12
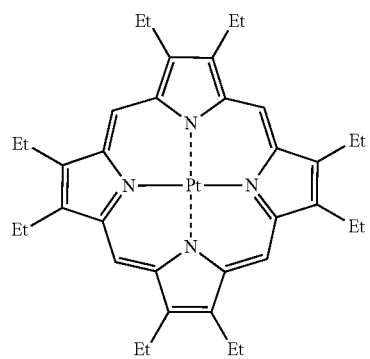
5-1
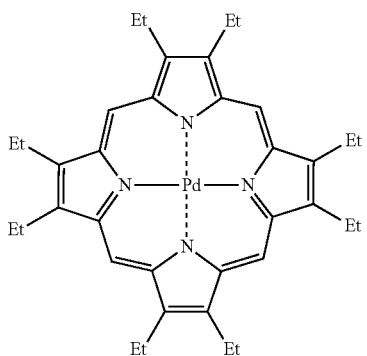
5-3
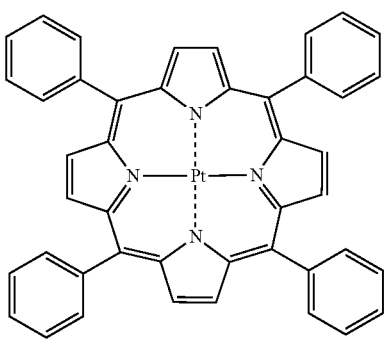
5-4
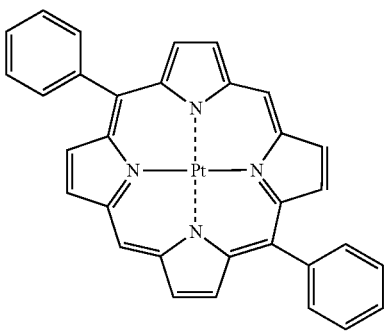
5-5
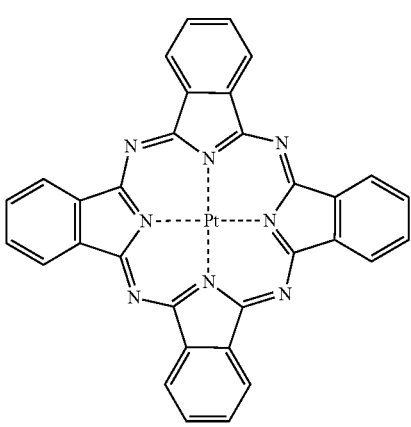
5-6

5-7

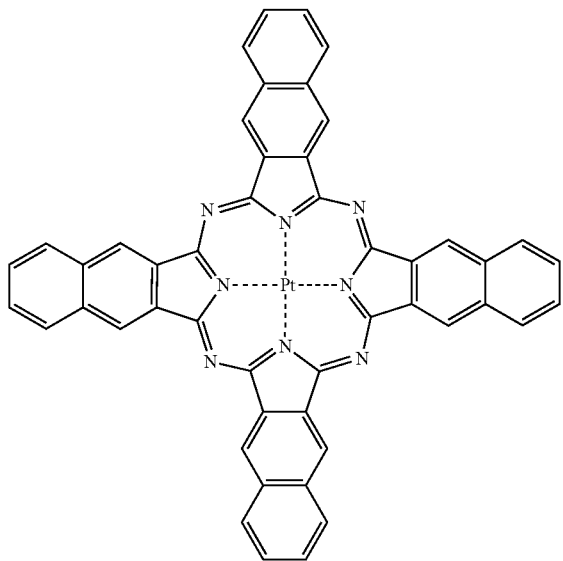

The content of the aforementioned phosphorescent dopant in the light-emitting layer is in the range of 1-20 wt %, preferably in the range of 5-10 wt %. The content of the host material in the light-emitting layer is 50 wt % or more, preferably in the range of 90-95 wt %.

The process for forming a light-emitting layer is not specifically limited and a material containing a phosphorescent dopant and a host material is dissolved in a solvent and the solution is formed into thin film by a wet process such as spin coating and inkjet technology or the material is formed into thin film by a dry process such as vacuum deposition.

The organic electroluminescent device of this invention comprises the aforementioned light-emitting layer between an anode and a cathode piled one upon another on a substrate. It is sufficient as long as the organic electroluminescent device is constructed of the substrate, the anode, the cathode, and the light-emitting layer and, preferably, a hole-injecting/transporting layer is disposed between the anode and the light-emitting layer and an electron-injecting/transporting layer is disposed between the cathode and the light-emitting layer.

The structure of the organic EL device of this invention will be explained next with reference to the drawing, but the structure of the device is not limited to the one illustrated in the drawing.

FIG. 1 schematically shows an example of the structure of an organic EL device generally used in this invention and the symbols in FIG. 1 stand for the following: 1 for a substrate, 2 for an anode, 3 for a hole-injecting layer, 4 for a hole-transporting layer, 5 for a light-emitting layer, 6 for an electron-transporting layer, and 7 for a cathode. The organic EL device of this invention comprises a substrate, an anode, a light-emitting layer, and a cathode as essential layers; in addition, the device preferably contains a hole-injecting/transporting layer and an electron-injecting/transporting layer and, further, a hole-blocking layer disposed between the light-emitting layer and the electron-injecting/transporting layer. The term hole-injecting/transporting layer means a hole-injecting layer and/or a hole-transporting layer while the term electron-injecting/transporting layer means an electron-injecting layer and/or an electron-transporting layer.

It is possible to build a structure that is the reverse of the structure shown in FIG. 1 by piling the cathode 7, the electron-transporting layer 6, the light-emitting layer 5, the hole-transporting layer 4, and the anode 2 one upon another in this order on the substrate 1. As described earlier, it is also possible to dispose the organic EL device of this invention between two substrates at least one of which is highly transparent. In this case of the reverse structure, it is possible to add or omit a layer or layers as needed.

The substrate 1 serves as a support for an organic EL device and the materials useful therefor include a quartz plate, a glass plate, a metal sheet, a metal foil, a plastic film, and a plastic sheet. In particular, a glass plate is preferred.

The anode 2 plays a role of injecting holes into the hole-injecting layer 3. The anode 2 is usually constructed of a metal such as aluminum, gold, silver, nickel, palladium, and platinum, a metal oxide such as an oxide of indium and/or tin (ITO), a metal halide such as copper iodide, carbon black, or an electrically conductive polymer such as poly(3-methylthiophene), polypyrrole, and polyaniline.

The light-emitting layer 5 is constituted of a light-emitting substance that emits light when excited by recombination of holes injected from the anode 2 and migrating through the hole-transporting layer 4 and electrons injected from the cathode 7 and migrating through the electron-transporting layer 6 upon application of an electrical field to the electrodes. The light-emitting layer 5 comprises the aforementioned dopant material and host material as a light-emitting substance.

The cathode 7 plays a role of injecting electrons through the electron-transporting layer 6 into the light-emitting layer 5. The materials useful for the cathode 7 are preferably metals of low work function for efficient injection of electrons and examples include metals such as tin, magnesium, indium, calcium, cesium, aluminum, and silver and alloys thereof. Examples of the alloys include magnesium-silver alloys, magnesium-indium alloys, and aluminum-lithium alloys.

The hole-injecting layer 3, the hole-transporting layer 4, and the electron-transporting layer 6 are optional organic layers; the hole-injecting layer 3 is used for the purpose of enhancing the efficiency of injecting holes into the hole-transporting layer 4 while the hole-transporting layer 4 and the electron-transporting layer 6 transport respectively holes and electrons to the light-emitting layer 5. It is allowable to dispose an electron-injecting layer between the cathode 7 and the electron-transporting layer 6. The materials useful for these layers are well known.

The materials for the hole-injecting layer include phthalocyanine compounds such as copper phthalocyanine (CuPC), organic compounds such as polyaniline and polythiophene, and oxides of metals such as vanadium, ruthenium, and molybdenum.

The materials for the hole-transporting layer include triazole derivatives, oxadiazole derivatives, imidazole derivatives, polyarylalkane derivatives, pyrazoline derivatives, pyrazolone derivatives, phenylenediamine derivatives, arylamine derivatives such as NPB, amino-substituted chalcone derivatives, oxazole derivatives, styrylanthracene derivatives, fluorenone derivatives, hydrazone derivatives, stilbene derivatives, silazan derivatives, aniline-based copolymers, and electrically conductive oligomers, typically thiophene oligomers.

The materials for the electron-transporting layer include metal complexes such as Alq3, 10-hydroxybenzo[h]quinoline metal complexes, oxadiazole derivatives, distyrylbiphenyl derivatives, silole derivatives, 3- or 5-hydroxyflavone metal complexes, benzoxazole metal complexes, benzothiazole metal complexes, trisbenzimidazolybenzene, quinoxaline compounds, phenanthroline derivatives, 2-t-butyl-9,10-N,N'-dicyanoanthraquinonediimine, n-type hydrogenated amorphous silicon carbide, n-type zinc sulfide, and n-type zinc selenide.

It is possible to build a structure that is the reverse of the structure shown in FIG. 1 by piling the cathode 7, the electron-transporting layer 6, the light-emitting layer 5, the hole-transporting layer 4, and the anode 2 one upon another in this order on the substrate 1. As described earlier, it is also possible to dispose the organic EL device of this invention between two substrates at least one of which is highly transparent. In this case of the reverse structure, it is possible to add or omit a layer or layers as needed.

The organic EL device of this invention is applicable to a single device, a device with its structure arranged in array, or a device in which the anode and the cathode are arranged in X-Y matrix. This invention provides an organic EL device that is enhanced in the luminous efficiency and markedly improved in the driving stability compared with the conventional devices utilizing emission of light from the excited singlet state by incorporating a compound of a specified skeleton and a phosphorescent dopant in the light-emitting layer and the device can perform excellently in applications to full-color or multicolor panels.

EXAMPLES

This invention will be explained in more detail below with reference to the examples, but it will not be limited to these examples.

Example 1

An organic EL device constituted as in FIG. 1 with addition of an electron-injecting layer was fabricated. Applying the vacuum deposition process at a degree of vacuum of $4.0 \times 10^{-4}$ Pa, the constituent layers were deposited in thin film one upon another on a glass substrate on which a 110 nm-thick ITO anode had been formed. First, CuPC was deposited on the ITO anode to a thickness of 30 nm as a hole-injecting layer and NPB was deposited to a thickness of 50 nm as a hole-transporting layer.

Then, a light-emitting layer was formed on the hole-transporting layer by co-depositing illustrated Compound 1-1, illustrated Compound 2-1, and illustrated Compound 3-1 as a host material and $Ir(piq)_2acac$ (illustrated Compound 4-8) as a dopant from different evaporation sources to a thickness of 40 nm. At this point, the co-deposition was performed under such conditions as to control the concentration of $Ir(piq)_2acac$ at 6.0 wt % and the weight ratio illustrated Compound 1-1: illustrated Compound 2-1:illustrated Compound 3-1 at 1:1:1. Then Alq3 was deposited to a thickness of 37.5 nm as an electron-transporting layer. Further, lithium fluoride (LiF) was deposited on the electron-transporting layer to a thickness of 0.5 nm as an electron-injecting layer. Finally, aluminum (Al) as an electrode was deposited on the electron-injecting layer to a thickness of 170 nm to complete the fabrication of the organic EL device.

The organic EL device thus fabricated was connected to an outside power source and, when direct current voltage was applied, the device was confirmed to emit light with the characteristics shown in Table 1. In Table 1, the luminance, voltage, and luminous efficiency were measured at 10 $mA/cm^2$. The luminance half life at an initial luminance of 1,000 $cd/m^2$ is shown in Table 1. The maximum wavelength of the spectrum of light emitted from the device was 620 nm and this proves that light is emitted from $Ir(piq)_2acac$.

Examples 2-13

Organic EL devices were fabricated as in Example 1 with the exception of changing the host materials incorporated in the light-emitting layer as shown in Table 1 and their luminous characteristics and luminance half life were evaluated. The vacuum deposition of the compounds of general formulas (1), (2), and (3) was performed under such conditions as to control the weight ratio after the vacuum deposition at 1:1 when two kinds were used or at 1:1:1 when three kinds were used. The results are shown in Table 1. The maximum wavelength of the spectrum of light emitted from the device was 620 nm and this proves that light is emitted from $Ir(piq)_2acac$.

Comparative Examples 1-3

Organic EL devices were fabricated as in Example 1 with the exception of using respectively illustrated Compound 1-1, illustrated Compound 2-1, and illustrated Compound 3-1 singly as a host material and their luminous characteristics and luminance half life were evaluated. The results are shown in Table 1.

TABLE 1

| | Host material (Compound No.) | | | Initial luminance (cd/m²) | Voltage (V) | Luminous efficiency (lm/W) | Luminance half life (h) |
|---|---|---|---|---|---|---|---|
| Example | | | | | | | |
| 1 | 1-1 | 2-1 | 3-1 | 945 | 7.3 | 4.1 | 7900 |
| 2 | 1-1 | | 3-1 | 602 | 7.3 | 2.6 | 6400 |
| 3 | 1-1 | | 3-2 | 600 | 7.0 | 2.7 | 5600 |
| 4 | 1-1 | | 3-3 | 491 | 7.6 | 2.0 | 5600 |
| 5 | 1-1 | 2-1 | | 582 | 7.2 | 2.5 | 5487 |
| 6 | 1-1 | 2-2 | | 663 | 7.7 | 2.4 | 7400 |
| 7 | 1-1 | 2-3 | | 685 | 7.5 | 2.9 | 6700 |
| 8 | 1-1 | 2-4 | | 420 | 7.3 | 1.6 | 5800 |
| 9 | 1-4 | 2-1 | | 629 | 7.4 | 2.7 | 6200 |
| 0 | 1-5 | 2-1 | | 736 | 8.0 | 2.9 | 8200 |
| 11 | 1-2 | 2-1 | | 1017 | 8.1 | 3.9 | 10100 |
| 12 | 1-2 | 2-2 | | 976 | 8.3 | 3.7 | 7800 |
| 13 | 1-8 | 2-1 | | 904 | 8.0 | 3.6 | 5500 |
| Comparative example | | | | | | | |
| 1 | 1-1 | | | 371 | 7.1 | 1.6 | 6100 |
| 2 | | 2-1 | | 1240 | 9.1 | 4.3 | 5500 |
| 3 | | | 3-1 | 913 | 8.0 | 3.6 | 1200 |

Example 14

An organic EL device constituted as in FIG. 1 with addition of an electron-injecting layer was fabricated. Applying the vacuum deposition process at a degree of vacuum of $4.0 \times 10^{-4}$ Pa, the constituent layers were deposited in thin film one upon another on a glass substrate on which a 110 nm-thick ITO anode had been formed. First, CuPC was deposited on the ITO anode to a thickness of 30 nm as a hole-injecting layer and then NPB was deposited to a thickness of 50 nm as a hole-transporting layer.

Next, a light-emitting layer was formed on the hole-transporting layer by co-depositing illustrated Compound 2-1 and illustrated Compound 3-1 as a host material and $Ir(piq)_2acac$ (illustrated Compound 4-8) as a dopant from different evaporation sources to a thickness of 40 nm. At this point, the co-deposition was performed under such conditions as to control the concentration of Ir(piq)$_2$acac at 6.0 wt % and the weight ratio illustrated Compound 2-1:illustrated Compound 3-1 at 1:1. Then Alq3 was deposited to a thickness of 37.5 nm as an electron-transporting layer. Further, lithium fluoride (LiF) was deposited on the electron-transporting layer to a thickness of 0.5 nm as an electron-injecting layer. Finally, aluminum (Al) as an electrode was deposited on the electron-injecting layer to a thickness of 170 nm to complete the fabrication of the organic EL device.

The organic EL device thus fabricated was connected to an outside power source and, when direct current voltage was applied, the device was confirmed to emit light with the characteristics shown in Table 2. In Table 2, the luminance, voltage, and luminous efficiency were measured at 10 mA/cm$^2$. The luminance half life at an initial luminance of 1,000 cd/m$^2$ is shown in Table 2. The maximum wavelength of the spectrum of light emitted from the device was 620 nm and this proves that light is emitted from Ir(piq)$_2$acac.

Examples 15-19

Organic EL devices were fabricated as in Example 14 with the exception of changing the host materials as shown in Table 2 and their luminous characteristics and luminance half life were evaluated. The vacuum deposition of the compounds of general formulas (2) and (3) was performed under such conditions as to control the weight ratio after the vacuum deposition at 1:1. The results are shown in Table 2. The maximum wavelength of the spectrum of light emitted from the device was 620 nm and this proves that light is emitted from Ir(piq)$_2$acac.

TABLE 2

| Example | Host material (Compound No.) | | Initial luminance (cd/m$^2$) | Voltage (V) | Luminous efficiency (lm/W) | Luminance half life (h) |
| --- | --- | --- | --- | --- | --- | --- |
| 14 | 2-1 | 3-1 | 1064 | 7.9 | 4.2 | 7800 |
| 15 | 2-2 | 3-1 | 924 | 8.0 | 3.6 | 7500 |
| 16 | 2-1 | 3-2 | 891 | 7.6 | 3.7 | 5900 |
| 17 | 2-2 | 3-3 | 905 | 8.4 | 3.4 | 6100 |
| 18 | 2-4 | 3-3 | 950 | 8.3 | 3.6 | 5600 |
| 19 | 2-3 | 3-1 | 985 | 8.3 | 3.7 | 6300 |

INDUSTRIAL APPLICABILITY

The organic EL device of this invention is capable of emitting light of high luminance at high efficiency with application of low voltage. Hence, the device is of high technical value because of its potential applicability to flat panel displays (for example, in office computers and wall-hanging television sets), vehicle-mounted display devices, mobile phone displays, light sources utilizing the characteristics of planar light emitters (for example, light sources for copiers and backlight sources of liquid crystal displays and instruments), signboards, and beacon lights.

The invention claimed is:

1. An organic electroluminescent device, comprising:
a light-emitting layer between an anode and a cathode piled one upon another on a substrate wherein the said light-emitting layer comprises (A) a phosphorescent dopant whose emission peak wavelength is longer than 600 nm and (B) a host material and the said host material comprises (b1) a compound represented by the following general formula (1) and a compound represented by the following general formula (3):

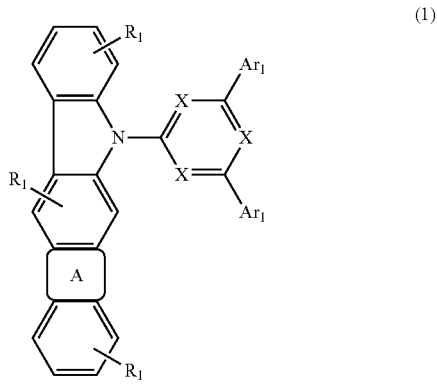

(1)

(1a)

wherein ring A is a heterocyclic ring fused to the adjacent rings and represented by formula (1a); X is independently CR or N and at least one of Xs is N; Ar$_1$ is independently (i) an aromatic hydrocarbon group selected from the group consisting of a phenyl group, a naphthyl group, a phenanthryl group, and an anthracenyl group or (ii) an aromatic heterocyclic group selected from the group consisting of a pyridyl group, a pyrimidyl group, a triazyl group, an imidazolyl group, a thienyl group, and a carbazolyl group, wherein the aromatic hydrocarbon group or the aromatic heterocyclic group is optionally substituted with substituents selected from the group consisting of an alkyl group of 1 to 6 carbon atoms, an alkoxyl group of 1 to 6 carbon atoms, an aryloxy group of 6 to 12 carbon atoms, an alkylthio group, a substituted amino group, an acetyl group, a phenyl group, a biphenylyl group, a terphenylyl group, a naphthyl group, a pyridyl group, a pyrimidyl group, a triazyl group, an imidazolyl group, a thienyl group, and a carbazolyl group; each of R and R$_1$ is independently hydrogen, an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an aryloxy group, an alkylthio group, an alkylsulfonyl group, a haloalkyl group, a hydroxyl group, an amide group, or an aromatic hydrocarbon group of 6 to 24 carbon atoms or an aromatic heterocyclic group of 3 to 24 carbon atoms, wherein the aromatic hydrocarbon group or the aromatic heterocyclic group is optionally substituted;

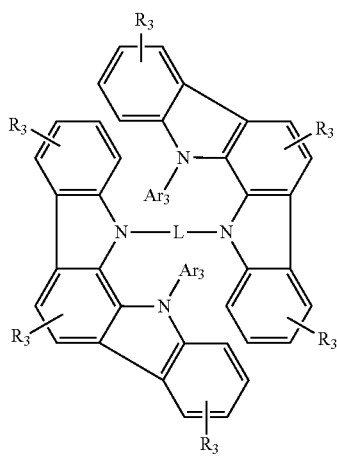

(3)

wherein $Ar_3$ is independently an aromatic hydrocarbon group of 6 to 24 carbon atoms or an aromatic heterocyclic group of 3 to 24 carbon atoms, wherein the aromatic hydrocarbon group or the aromatic heterocyclic group is optionally substituted; L is a divalent aromatic hydrocarbon group of 6 to 24 carbon atoms or an aromatic heterocyclic group of 3 to 24 carbon atoms, wherein the aromatic hydrocarbon group or the aromatic heterocyclic group is optionally substituted; $R_3$ is independently hydrogen, an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an aryloxy group, an alkylthio group, an alkylsulfonyl group, a haloalkyl group, a hydroxyl group, an amide group, or an aromatic hydrocarbon group of 6 to 24 carbon atoms or an aromatic heterocyclic group of 3 to 24 carbon atoms wherein the aromatic hydrocarbon group or the aromatic heterocyclic group is optionally substituted.

2. An organic electroluminescent device as described in claim 1, wherein the compound represented by general formula (1) is a compound represented by the following general formula (4):

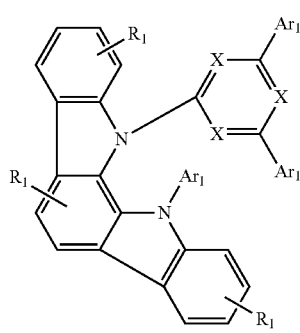

(4)

wherein X, $Ar_1$, and $R_1$ respectively have the same meaning as X, $Ar_1$, and $R_1$ in general formula (1).

* * * * *